(12) United States Patent
Benz et al.

(10) Patent No.: US 8,309,340 B2
(45) Date of Patent: Nov. 13, 2012

(54) INSULIN DEGRADING ENZYME CRYSTALS

(75) Inventors: Joerg Benz, Rheinfelden (DE); Dominique Burger, Riehen (CH); Martine Stihle, Michelbach-le-Bas (FR); Ralf Thoma, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 2 days.

(21) Appl. No.: 12/810,032

(22) PCT Filed: Dec. 22, 2008

(86) PCT No.: PCT/EP2008/011031
§ 371 (c)(1),
(2), (4) Date: Jun. 22, 2010

(87) PCT Pub. No.: WO2009/083224
PCT Pub. Date: Jul. 9, 2009

(65) Prior Publication Data
US 2010/0323427 A1 Dec. 23, 2010

(30) Foreign Application Priority Data
Dec. 27, 2007 (EP) .................................. 07150427

(51) Int. Cl.
*C12N 9/50* (2006.01)
*G01N 31/00* (2006.01)
(52) U.S. Cl. .......................................... 435/219; 436/4
(58) Field of Classification Search .................. None
See application file for complete search history.

(56) References Cited

FOREIGN PATENT DOCUMENTS
WO 02/24893 3/2002

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Shen Yeuquan et al: "Structures of human insulin-degrading enzyme reveal a new substrate recognition mechanism" Nature 443, 7113 (2006) 870-874 XP002526907.
Leissring Malcom et al: "Structural biology: enzyme target to latch on to." Nature (2006) 443:7113 761-762 XP002526908.
Im Hookang et al Structure of Substrate-Free Human Insulin-Degrading Enzyme (IDE) and Biophysical Analysis of ATP-induced conformational switch of IDE' Journal of Biolgoical Chemistry, (2007) 282:35 pgs. 25453-25463 XP002526909.
Database PDBSUM Malito, E & Tang, W.J., European Bioinformatics Institute: "Substrate-Free IDE Structure in its Closed Conformation" Database Accession 2jg4 XP002526910.
Database PDBSUM: Shen, H. Im, Tang, W. J, European Bioinformatics Institute; (2007) H: "Crystal structure of human insulin degrading enzyme complexed with co-purified peptides" Database Accession 2jbu, XP002526911.
(Translation of Jap Off Act in Corres Jap App 2010540066 Jul. 5, 2012).
Song et al., Journal of Biological Chemistry 279(52):54216-54220 (2004).

* cited by examiner

*Primary Examiner* — Suzanne M Noakes
(74) *Attorney, Agent, or Firm* — George W. Johnston; Dennis P. Tramaloni; Brian C. Remy

(57) ABSTRACT

The present invention provides apo crystals and co-crystals of insulin-degrading enzyme (IDE) and their uses in drug development.

4 Claims, No Drawings

SEQUENCE LISTING

<160> NUMBER OF SEQ ID NOS: 4

<210> SEQ ID NO 1
<211> LENGTH: 3131
<212> TYPE: DNA
<213> ORGANISM: Homo sapiens
<220> FEATURE:
<221> NAME/KEY: CDS
<222> LOCATION: (41)..(3097)

<400> SEQUENCE: 1

```
gaggaagcgt tgcggtgat cccggcgact gcgctggcta atg cgg tac cgg cta         55
                                              Met Arg Tyr Arg Leu
                                              1               5 gcg tgg ctt ctg cac ccc gca ctg ccc agc acc ttc cgc tca gtc ctc       103
Ala Trp Leu Leu His Pro Ala Leu Pro Ser Thr Phe Arg Ser Val Leu
         10                  15                  20 ggc gcc cgc ctg ccg cct ccg gag cgc ctg tgt ggt ttc caa aaa aag       151
Gly Ala Arg Leu Pro Pro Pro Glu Arg Leu Cys Gly Phe Gln Lys Lys
     25                  30                  35 act tac agc aaa atg aat aat cca gcc atc aag aga ata gga aat cac       199
Thr Tyr Ser Lys Met Asn Asn Pro Ala Ile Lys Arg Ile Gly Asn His
 40                  45                  50 att acc aag tct cct gaa gac aag cga gaa tat cga ggg cta gag ctg       247
Ile Thr Lys Ser Pro Glu Asp Lys Arg Glu Tyr Arg Gly Leu Glu Leu
         55                  60                  65 gcc aat ggt atc aaa gta ctt ctt atc agt gat ccc acc acg gat aag       295
Ala Asn Gly Ile Lys Val Leu Leu Ile Ser Asp Pro Thr Thr Asp Lys
 70                  75                  80                  85 tca tca gca gca ctt gat gtg cac ata ggt tca ttg tcg gat cct cca       343
Ser Ser Ala Ala Leu Asp Val His Ile Gly Ser Leu Ser Asp Pro Pro
             90                  95                 100 aat att gct ggc tta agt cat ttt tgt gaa cat atg ctt ttt ttg gga       391
Asn Ile Ala Gly Leu Ser His Phe Cys Glu His Met Leu Phe Leu Gly
        105                 110                 115 aca aag aaa tac cct aaa gaa aat gaa tac agc cag ttt ctc agt gag       439
Thr Lys Lys Tyr Pro Lys Glu Asn Glu Tyr Ser Gln Phe Leu Ser Glu
    120                 125                 130 cat gca gga agt tca aat gcc ttt act agt gga gag cat acc aat tac       487
His Ala Gly Ser Ser Asn Ala Phe Thr Ser Gly Glu His Thr Asn Tyr
        135                 140                 145 tat ttt gat gtt tct cat gaa cac cta gaa ggt gcc cta gac agg ttt       535
```

-continued

```
Tyr Phe Asp Val Ser His Glu His Leu Glu Gly Ala Leu Asp Arg Phe
150                 155                 160                 165 gca cag ttt ttt ctg tgc ccc ttg ttc gat gaa agt tgc aaa gac aga     583
Ala Gln Phe Phe Leu Cys Pro Leu Phe Asp Glu Ser Cys Lys Asp Arg
        170                 175                 180 gag gtg aat gca gtt gat tca gaa cat gag aag aat gtg atg aat gat     631
Glu Val Asn Ala Val Asp Ser Glu His Glu Lys Asn Val Met Asn Asp
            185                 190                 195 gcc tgg aga ctc ttt caa ttg gaa aaa gct aca ggg aat cct aaa cac     679
Ala Trp Arg Leu Phe Gln Leu Glu Lys Ala Thr Gly Asn Pro Lys His
                200                 205                 210 ccc ttc agt aaa ttt ggg aca ggt aac aaa tat act ctg gag act aga     727
Pro Phe Ser Lys Phe Gly Thr Gly Asn Lys Tyr Thr Leu Glu Thr Arg
            215                 220                 225 cca aac caa gaa ggc att gat gta aga caa gag cta ctg aaa ttc cat     775
Pro Asn Gln Glu Gly Ile Asp Val Arg Gln Glu Leu Leu Lys Phe His
230                 235                 240                 245 tct gct tac tat tca tcc aac tta atg gct gtt tgt gtt tta ggt cga     823
Ser Ala Tyr Tyr Ser Ser Asn Leu Met Ala Val Cys Val Leu Gly Arg
                250                 255                 260 gaa tct tta gat gac ttg act aat ctg gtg gta aag tta ttt tct gaa     871
Glu Ser Leu Asp Asp Leu Thr Asn Leu Val Val Lys Leu Phe Ser Glu
            265                 270                 275 gta gag aac aaa aat gtt cca ttg cca gaa ttt cct gaa cac cct ttc     919
Val Glu Asn Lys Asn Val Pro Leu Pro Glu Phe Pro Glu His Pro Phe
        280                 285                 290 caa gaa gaa cat ctt aaa caa ctt tac aaa ata gta ccc att aaa gat     967
Gln Glu Glu His Leu Lys Gln Leu Tyr Lys Ile Val Pro Ile Lys Asp
295                 300                 305 att agg aat ctc tat gtg aca ttt ccc ata cct gac ctt cag aaa tac    1015
Ile Arg Asn Leu Tyr Val Thr Phe Pro Ile Pro Asp Leu Gln Lys Tyr
310                 315                 320                 325 tac aaa tca aat cct ggt cat tat ctt ggt cat ctc att ggg cat gaa    1063
Tyr Lys Ser Asn Pro Gly His Tyr Leu Gly His Leu Ile Gly His Glu
                330                 335                 340 ggt cct gga agt ctg tta tca gaa ctt aag tca aag ggc tgg gtt aat    1111
Gly Pro Gly Ser Leu Leu Ser Glu Leu Lys Ser Lys Gly Trp Val Asn
            345                 350                 355 act ctt gtt ggt ggg cag aag gaa gga gcc cga ggt ttt atg ttt ttt    1159
Thr Leu Val Gly Gly Gln Lys Glu Gly Ala Arg Gly Phe Met Phe Phe
        360                 365                 370 atc att aat gtg gac ttg acc gag gaa gga tta tta cat gtt gaa gat    1207
Ile Ile Asn Val Asp Leu Thr Glu Glu Gly Leu Leu His Val Glu Asp
375                 380                 385 ata att ttg cac atg ttt caa tac att cag aag tta cgt gca gaa gga    1255
Ile Ile Leu His Met Phe Gln Tyr Ile Gln Lys Leu Arg Ala Glu Gly
390                 395                 400                 405 cct caa gaa tgg gtt ttc caa gag tgc aag gac ttg aat gct gtt gct    1303
Pro Gln Glu Trp Val Phe Gln Glu Cys Lys Asp Leu Asn Ala Val Ala
                410                 415                 420 ttt agg ttt aaa gac aaa gag agg cca cgg ggc tat aca tct aag att    1351
Phe Arg Phe Lys Asp Lys Glu Arg Pro Arg Gly Tyr Thr Ser Lys Ile
            425                 430                 435 gca gga ata ttg cat tat tat ccc cta gaa gag gtg ctc aca gcg gaa    1399
Ala Gly Ile Leu His Tyr Tyr Pro Leu Glu Glu Val Leu Thr Ala Glu
        440                 445                 450 tat tta ctg gaa gaa ttt aga cct gac tta ata gag atg gtt ctc gat    1447
Tyr Leu Leu Glu Glu Phe Arg Pro Asp Leu Ile Glu Met Val Leu Asp
455                 460                 465 aaa ctc aga cca gaa aat gtc cgg gtt gcc ata gtt tct aaa tct ttt    1495
```

-continued

| | | | | | | | | | | | | | | |
|---|---|---|---|---|---|---|---|---|---|---|---|---|---|---|
| Lys | Leu | Arg | Pro | Glu | Asn | Val | Arg | Val | Ala | Ile | Val | Ser | Lys | Ser | Phe |
| 470 | | | | 475 | | | | | 480 | | | | 485 | | |

```
gaa gga aaa act gat cgc aca gaa gag tgg tat gga acc cag tac aaa    1543
Glu Gly Lys Thr Asp Arg Thr Glu Glu Trp Tyr Gly Thr Gln Tyr Lys
            490                 495                 500 caa gaa gct ata ccg gat gaa gtc atc aag aaa tgg caa aat gct gac    1591
Gln Glu Ala Ile Pro Asp Glu Val Ile Lys Lys Trp Gln Asn Ala Asp
            505                 510                 515 ctg aat ggg aaa ttt aaa ctt cct aca aag aat gaa ttt att cct acg    1639
Leu Asn Gly Lys Phe Lys Leu Pro Thr Lys Asn Glu Phe Ile Pro Thr
            520                 525                 530 aat ttt gag att tta ccg tta gaa aaa gag gcg aca cca tac cct gct    1687
Asn Phe Glu Ile Leu Pro Leu Glu Lys Glu Ala Thr Pro Tyr Pro Ala
            535                 540                 545 ctt att aag gat aca gct atg agc aaa ctt tgg ttc aaa caa gat gat    1735
Leu Ile Lys Asp Thr Ala Met Ser Lys Leu Trp Phe Lys Gln Asp Asp
550             555                 560                 565 aag ttt ttt ttg ccg aag gct tgt ctc aac ttt gaa ttt ttc agc cca    1783
Lys Phe Phe Leu Pro Lys Ala Cys Leu Asn Phe Glu Phe Phe Ser Pro
                570                 575                 580 ttt gct tat gtg gac ccc ttg cac tgt aac atg gcc tat ttg tac ctt    1831
Phe Ala Tyr Val Asp Pro Leu His Cys Asn Met Ala Tyr Leu Tyr Leu
                585                 590                 595 gag ctc ctc aaa gac tca ctc aac gag tat gca tat gca gca gag cta    1879
Glu Leu Leu Lys Asp Ser Leu Asn Glu Tyr Ala Tyr Ala Ala Glu Leu
                600                 605                 610 gca ggc ttg agc tat gat ctc caa aat acc atc tat ggg atg tat ctt    1927
Ala Gly Leu Ser Tyr Asp Leu Gln Asn Thr Ile Tyr Gly Met Tyr Leu
            615                 620                 625 tca gtg aaa ggt tac aat gac aag cag cca att tta cta aag aag att    1975
Ser Val Lys Gly Tyr Asn Asp Lys Gln Pro Ile Leu Leu Lys Lys Ile
630             635                 640                 645 att gag aaa atg gct acc ttt gag att gat gaa aaa aga ttt gaa att    2023
Ile Glu Lys Met Ala Thr Phe Glu Ile Asp Glu Lys Arg Phe Glu Ile
                650                 655                 660 atc aaa gaa gca tat atg cga tct ctt aac aat ttc cgg gct gaa cag    2071
Ile Lys Glu Ala Tyr Met Arg Ser Leu Asn Asn Phe Arg Ala Glu Gln
                665                 670                 675 cct cac cag cat gcc atg tac tac ctc cgc ttg ctg atg act gaa gtg    2119
Pro His Gln His Ala Met Tyr Tyr Leu Arg Leu Leu Met Thr Glu Val
            680                 685                 690 gcc tgg act aaa gat gag tta aaa gaa gct ctg gat gat gta acc ctt    2167
Ala Trp Thr Lys Asp Glu Leu Lys Glu Ala Leu Asp Asp Val Thr Leu
695             700                 705 cct cgc ctt aag gcc ttc ata cct cag ctc ctg tca cgg ctg cac att    2215
Pro Arg Leu Lys Ala Phe Ile Pro Gln Leu Leu Ser Arg Leu His Ile
710             715                 720                 725 gaa gcc ctt ctc cat gga aac ata aca aag cag gct gca tta gga att    2263
Glu Ala Leu Leu His Gly Asn Ile Thr Lys Gln Ala Ala Leu Gly Ile
                730                 735                 740 atg cag atg gtt gaa gac acc ctc att gaa cat gct cat acc aaa cct    2311
Met Gln Met Val Glu Asp Thr Leu Ile Glu His Ala His Thr Lys Pro
                745                 750                 755 ctc ctt cca agt cag ctg gtt cgg tat aga gaa gtt cag ctc cct gac    2359
Leu Leu Pro Ser Gln Leu Val Arg Tyr Arg Glu Val Gln Leu Pro Asp
            760                 765                 770 aga gga tgg ttt gtt tat cag cag aga aat gaa gtt cac aat aac tgt    2407
Arg Gly Trp Phe Val Tyr Gln Gln Arg Asn Glu Val His Asn Asn Cys
            775                 780                 785 ggc atc gag ata tac tac caa aca gac atg caa agc acc tca gag aat    2455
```

| | | | | | | | | | | | | |
|---|---|---|---|---|---|---|---|---|---|---|---|---|
| Gly | Ile | Glu | Ile | Tyr | Tyr | Gln | Thr | Asp | Met | Gln | Ser | Thr | Ser | Glu | Asn |
| 790 | | | | 795 | | | | 800 | | | | 805 | | | |

```
atg ttt ctg gag ctc ttc tgt cag att atc tcg gaa cct tgc ttc aac      2503
Met Phe Leu Glu Leu Phe Cys Gln Ile Ile Ser Glu Pro Cys Phe Asn
            810                 815                 820 acc ctg cgc acc aag gag cag ttg ggc tat atc gtc ttc agc ggg cca      2551
Thr Leu Arg Thr Lys Glu Gln Leu Gly Tyr Ile Val Phe Ser Gly Pro
        825                 830                 835 cgt cga gct aat ggc ata cag ggc ttg aga ttc atc atc cag tca gaa      2599
Arg Arg Ala Asn Gly Ile Gln Gly Leu Arg Phe Ile Ile Gln Ser Glu
    840                 845                 850 aag cca cct cac tac cta gaa agc aga gtg gaa gct ttc tta att acc      2647
Lys Pro Pro His Tyr Leu Glu Ser Arg Val Glu Ala Phe Leu Ile Thr
855                 860                 865 atg gaa aag tcc ata gag gac atg aca gaa gag gcc ttc caa aaa cac      2695
Met Glu Lys Ser Ile Glu Asp Met Thr Glu Glu Ala Phe Gln Lys His
870                 875                 880                 885 att cag gca tta gca att cgt cga cta gac aaa cca aag aag cta tct      2743
Ile Gln Ala Leu Ala Ile Arg Arg Leu Asp Lys Pro Lys Lys Leu Ser
            890                 895                 900 gct gag tgt gct aaa tac tgg gga gaa atc atc tcc cag caa tat aat      2791
Ala Glu Cys Ala Lys Tyr Trp Gly Glu Ile Ile Ser Gln Gln Tyr Asn
        905                 910                 915 ttt gac aga gat aac act gag gtt gca tat tta aag aca ctt acc aag      2839
Phe Asp Arg Asp Asn Thr Glu Val Ala Tyr Leu Lys Thr Leu Thr Lys
    920                 925                 930 gaa gat atc atc aaa ttc tac aag gaa atg ttg gca gta gat gct cca      2887
Glu Asp Ile Ile Lys Phe Tyr Lys Glu Met Leu Ala Val Asp Ala Pro
935                 940                 945 agg aga cat aag gta tcc gtc cat gtt ctt gcc agg gaa atg gat tct      2935
Arg Arg His Lys Val Ser Val His Val Leu Ala Arg Glu Met Asp Ser
950                 955                 960                 965 tgt cct gtt gtt gga gag ttc cca tgt caa aat gac ata aat ttg tca      2983
Cys Pro Val Val Gly Glu Phe Pro Cys Gln Asn Asp Ile Asn Leu Ser
            970                 975                 980 caa gca cca gcc ttg cca caa cct gaa gtg att cag aac atg acc gaa      3031
Gln Ala Pro Ala Leu Pro Gln Pro Glu Val Ile Gln Asn Met Thr Glu
        985                 990                 995 ttc aag cgt ggt ctg cca ctg ttt  ccc ctt gtg aaa  cca cat att        3076
Phe Lys Arg Gly Leu Pro Leu Phe  Pro Leu Val Lys Pro  His Ile
    1000                 1005                 1010 aac ttc atg gct gca aaa ctc tgaagattcc ccatgcatgg gaaagtgcaa        3127
Asn Phe Met Ala Ala Lys Leu
            1015 gtgg                                                                3131

<210> SEQ ID NO 2
<211> LENGTH: 1019
<212> TYPE: PRT
<213> ORGANISM: Homo sapiens

<400> SEQUENCE: 2

Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
            20                  25                  30

Gly Phe Gln Lys Lys Thr Tyr Ser Lys Met Asn Asn Pro Ala Ile Lys
        35                  40                  45

Arg Ile Gly Asn His Ile Thr Lys Ser Pro Glu Asp Lys Arg Glu Tyr
    50                  55                  60
```

```
Arg Gly Leu Glu Leu Ala Asn Gly Ile Lys Val Leu Leu Ile Ser Asp
 65                  70                  75                  80

Pro Thr Thr Asp Lys Ser Ser Ala Ala Leu Asp Val His Ile Gly Ser
             85                  90                  95

Leu Ser Asp Pro Pro Asn Ile Ala Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
        130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

Gly Asn Pro Lys His Pro Phe Ser Lys Phe Gly Thr Gly Asn Lys Tyr
        210                 215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
        275                 280                 285

Pro Glu His Pro Phe Gln Glu Glu His Leu Lys Gln Leu Tyr Lys Ile
        290                 295                 300

Val Pro Ile Lys Asp Ile Arg Asn Leu Tyr Val Thr Phe Pro Ile Pro
305                 310                 315                 320

Asp Leu Gln Lys Tyr Tyr Lys Ser Asn Pro Gly His Tyr Leu Gly His
                325                 330                 335

Leu Ile Gly His Glu Gly Pro Gly Ser Leu Leu Ser Gly Leu Lys Ser
            340                 345                 350

Lys Gly Trp Val Asn Thr Leu Val Gly Gly Gln Lys Glu Gly Ala Arg
        355                 360                 365

Gly Phe Met Phe Phe Ile Ile Asn Val Asp Leu Thr Glu Glu Gly Leu
        370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
            420                 425                 430

Tyr Thr Ser Lys Ile Ala Gly Ile Leu His Tyr Tyr Pro Leu Glu Glu
        435                 440                 445

Val Leu Thr Ala Glu Tyr Leu Leu Glu Glu Phe Arg Pro Asp Leu Ile
        450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
```

-continued

```
                485                 490                 495
Gly Thr Gln Tyr Lys Gln Glu Ala Ile Pro Asp Glu Val Ile Lys Lys
                500                 505                 510

Trp Gln Asn Ala Asp Leu Asn Gly Lys Phe Lys Leu Pro Thr Lys Asn
                515                 520                 525

Glu Phe Ile Pro Thr Asn Phe Glu Ile Leu Pro Leu Glu Lys Glu Ala
            530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
                565                 570                 575

Glu Phe Phe Ser Pro Phe Ala Tyr Val Asp Pro Leu His Cys Asn Met
            580                 585                 590

Ala Tyr Leu Tyr Leu Glu Leu Leu Lys Asp Ser Leu Asn Glu Tyr Ala
            595                 600                 605

Tyr Ala Ala Glu Leu Ala Gly Leu Ser Tyr Asp Leu Gln Asn Thr Ile
        610                 615                 620

Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
                645                 650                 655

Lys Arg Phe Glu Ile Ile Lys Glu Ala Tyr Met Arg Ser Leu Asn Asn
            660                 665                 670

Phe Arg Ala Glu Gln Pro His Gln His Ala Met Tyr Tyr Leu Arg Leu
            675                 680                 685

Leu Met Thr Glu Val Ala Trp Thr Lys Asp Glu Leu Lys Glu Ala Leu
        690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Ile Met Gln Met Val Glu Asp Thr Leu Ile Glu His
            740                 745                 750

Ala His Thr Lys Pro Leu Leu Pro Ser Gln Leu Val Arg Tyr Arg Glu
        755                 760                 765

Val Gln Leu Pro Asp Arg Gly Trp Phe Val Tyr Gln Arg Asn Glu
        770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
                805                 810                 815

Glu Pro Cys Phe Asn Thr Leu Arg Thr Lys Glu Gln Leu Gly Tyr Ile
            820                 825                 830

Val Phe Ser Gly Pro Arg Ala Asn Gly Ile Gln Gly Leu Arg Phe
            835                 840                 845

Ile Ile Gln Ser Glu Lys Pro Pro His Tyr Leu Glu Ser Arg Val Glu
        850                 855                 860

Ala Phe Leu Ile Thr Met Glu Lys Ser Ile Glu Asp Met Thr Glu Glu
865                 870                 875                 880

Ala Phe Gln Lys His Ile Gln Ala Leu Ala Ile Arg Arg Leu Asp Lys
                885                 890                 895

Pro Lys Lys Leu Ser Ala Glu Cys Ala Lys Tyr Trp Gly Glu Ile Ile
            900                 905                 910
```

-continued

```
Ser Gln Gln Tyr Asn Phe Asp Arg Asp Asn Thr Glu Val Ala Tyr Leu
        915                 920                 925

Lys Thr Leu Thr Lys Glu Asp Ile Ile Lys Phe Tyr Lys Glu Met Leu
    930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Cys Gln Asn
                965                 970                 975

Asp Ile Asn Leu Ser Gln Ala Pro Ala Leu Pro Gln Pro Glu Val Ile
                980                 985                 990

Gln Asn Met Thr Glu Phe Lys Arg  Gly Leu Pro Leu Phe  Pro Leu Val
        995                 1000                1005

Lys Pro  His Ile Asn Phe Met  Ala Ala Lys Leu
    1010                1015

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccatatgaa taatccagcc atcaagag                                            28

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctgcggccg ctcagagttt tgcagccatg                                          30
```

INSULIN DEGRADING ENZYME CRYSTALS

This application is the National Stage of International Application No. PCT/EP2008/011031, filed Dec. 22, 2008, which claims the benefit of EP 07150427.8 filed Dec. 27, 2007, which is hereby incorporated by reference in its entirety.

TABLES

The instant application contains Tables 3-4s which have been submitted in ASCII format via EFS-Web and are hereby incorporated by reference in its entirety. Said ANSI copy, created on Aug. 15, 2012, is named CD_24581_Tables.txt and is 2700 kilobytes in size.

SEQUENCE LISTING

The instant application contains a Sequence Listing which has been submitted in ASCII format via EFS-Web and is hereby incorporated by reference in its entirety. Said ASCII copy, created on Aug. 24, 2010, is named 24581.txt, and is 24,687 bytes in size.

The present invention relates to crystals of insulin-degrading enzyme (IDE) in apo-form and with ligand and to the three-dimensional X-ray crystal structure derived thereof.

Insulin-degrading enzyme (IDE) is a $Zn^{2+}$-metalloprotease with a molecular weight of 113 kDa. The active site signature sequence of IDE consists of His-Glu-aa-aa-His (HEXXH) in which the two histidines coordinate the binding of the zinc ion and the glutamate plays an essential role in catalysis. IDE is ubiquitously expressed with its highest expression in the liver, testes, muscle and brain. IDE is abundant in the cytosol and peroxisomes and is also found in the rough endoplasmatic reticulum.

The gene encoding IDE is located on chromosome 10q23-q25 in humans. It spans approximately 120 kb and contains 24 exons. The coding sequence is highly conserved during evolution from *E. coli*, to Drosophila, to human.

IDE has been shown to play role in the degradation and clearance of insulin in vivo. Furthermore, IDE shows a degradation potential for some peptidic hormones and for amyloid-? peptide. Overexpression of IDE in cells in culture has been found to increase the rate of insulin degradation. The GK rat is an animal model of type 2 diabetes. IDE gene mutations are the genetic cause of diabetes in these animals. The mutated form of IDE expressed in these rats increases insulin levels as a result of reduced insulin degradation, and causes symptoms typical of human type 2 diabetes syndrome.

It has been shown that IDE is capable of degrading amyloid-β (Aβ). Aβ is neurotoxic and its accumulation results in amyloid fibril formation and the generation of senile plaques, the hallmark of Alzheimer's disease. It was suggested that IDE is involved in the clearance of A? from the brain and cerobrospinal fluid (CSF) and thereby preventing the formation of senile plaques. The mapping of the IDE gene to chromosome 10q23-q25 made it a candidate gene for the Alzheimer disease-6 locus.

The involvement of IDE in the pathogenesis of type 2 diabetes and Alzheimer disease makes it an attractive target for the development of drugs for the treatment of type 2 diabetes and Alzheimer disease.

It is a first object of the present invention to provide an apo crystal of an insulin-degrading enzyme (IDE) polypeptide, wherein the crystal belongs to space group $P2_1$. The DNA sequence of human IDE (hIDE) is set forth in Seq. Id. No. 1 and the amino acid sequence of human IDE polypeptide is set forth in Seq. Id. No. 2.

In a preferred embodiment, the apo crystal has unit cell dimensions of a=78±3 Å, b=115±3 Å, c=124±3 Å, β=97±3°.

In a second object, the present invention relates to a co-crystal of an IDE polypeptide and an allosteric ligand, wherein the crystal belongs to space group $P2_1$.

In a preferred embodiment, the co-crystal has unit cell dimensions of a=78±3 Å, b=115±3 Å, c=124±3 Å, β=97±3°.

In another preferred embodiment of the co-crystal, the allosteric ligand is 1H-Indole-7-carboxylic acid (3-chlorophenyl)-amide.

In a preferred embodiment of the apo crystals or the co-crystals of the present invention, the IDE polypeptide is a polypeptide having a sequence similarity to a polypeptide of Seq. Id. No. 2 of at least 80%, preferably at least 85%, more preferably at least 90%, even more preferably at least 95%, most preferably 100%.

In a further preferred embodiment of the apo crystals or co-crystals of the present invention, the IDE polypeptide comprises amino acids 43-1018 of Seq. Id. No. 2.

In a fourth object the present invention relates to a method of crystallizing an IDE polypeptide, the method comprising: providing an aqueous solution of the IDE polypeptide, and growing crystals by vapor diffusion or microbatch using a buffered reservoir solution of 5% to 30% (w/v) PEG and 5-15% ethylene glycol, wherein the PEG has an average molecular weight of 200 Da to 10 kDa. Preferably the PEG is PEG 5000 MME. The ethylene glycol concentration is preferably about 10% (w/w).

In a fifth object the present invention relates to a method for co-crystallizing an IDE polypeptide with a ligand, the method comprising: providing an aqueous solution of the polypeptide, adding a molar excess of the ligand to the aqueous solution of the polypeptide, and growing crystals by vapor diffusion or microbatch using a buffered reservoir solution of 0% to 30% (w/v) PEG and 5-15% ethylene glycol, wherein the PEG has an average molecular weight of 200 Da to 5 kDa. Preferably about 20% PEG1500 and about 4% PEG400 are used to co-crystallize an IDE polypeptide with a ligand.

In a preferred embodiment of the method of crystallizing an IDE polypeptide or a method for co-crystallizing an IDE polypeptide with a ligand, the IDE polypeptide is a polypeptide having a sequence similarity to a polypeptide of Seq. Id. No. 2 of at least 80%, preferably at least 85%, more preferably at least 90%, even more preferably at least 95%, most preferably 100%. A preferred IDE polypeptide for use in the methods of the present invention comprises amino acids 43-1018 of Seq. Id. No. 2.

In a sixth object the present invention provides a method for identifying a compound that can bind to an allosteric site of an IDE polypeptide comprising the steps:

a) determining the allosteric site of the IDE polypeptide from the three dimensional model of the IDE polypeptide using the atomic coordinates of Table 4± a root mean square deviation from the backbone atoms of said amino acids of not more than 2 Å; and b) performing computer fitting analysis to identify a compound that can bind to the IDE allosteric site.

In a preferred embodiment, the method comprises the steps: generating a three dimensional model of the allosteric site of IDE using the relative structural data coordinates of Table 4 of residues L201, F202, Q203, L204, K205, T208, Y302, I304, Y314, V315, T316, F317, E364, I374, N376, R472, V478, A479, V481± a root mean square deviation from the backbone atoms of said amino acids of not more than 2 Å; and performing computer fitting analysis to identify an allosteric ligand of IDE.

In a seventh object, the present invention provides an apo crystal or co-crystal of an IDE polypeptide having the structure defined by the coordinates of Table 3 or Table 4, optionally varied by an rmsd of less than 2.0 Å.

Crystals of the present invention can be grown by a number of techniques including batch crystallization, vapour diffusion (either by sitting drop or hanging drop) and by microdialysis. Seeding of the crystals in some instances is required to obtain X-ray quality crystals. Standard micro- and/or macro-seeding of crystals may therefore be used.

In a preferred embodiment of the invention, crystals are grown by vapor diffusion. In this method, the polypeptide solution is allowed to equilibrate in a closed container with a larger aqueous reservoir having a precipitant concentration optimal for producing crystals. Generally, less than about 10 l of substantially pure polypeptide solution is mixed with an equal or similar volume of reservoir solution, giving a precipitant concentration about half that required for crystallization. This solution is suspended as a droplet underneath a coverslip, which is sealed onto the top of a reservoir. The sealed container is allowed to stand, from one day to one year, usually for about 2-6 weeks, until crystals grow.

Methods for obtaining the three-dimensional structure of the crystals described herein, as well as the atomic structure coordinates, are well-known in the art (see, e.g., D. E. McRee, Practical Protein Crystallography, published by Academic Press, San Diego (1993), and references cited therein).

The crystals of the invention, and particularly the atomic structure coordinates obtained therefrom, have a wide variety of uses. For example, the crystals and structure coordinates described herein are particularly useful for identifying compounds that bind to IDE proteins as an approach towards developing new therapeutic agents.

The structure coordinates described herein can be used as phasing models in determining the crystal structures of additional native or mutated, as well as the structures of co-crystals of IDE polypeptides with bound ligand. The structure coordinates, as well as models of the three-dimensional structures obtained therefrom, can also be used to aid the elucidation of solution-based structures of native or mutated IDE polypeptide, such as those obtained via NMR.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of IDE polypeptide or an active binding site thereof, as defined by the structure coordinates of IDE polypeptide described herein.

Molecular docking of large compound databases to target proteins of known or modelled 3-dimensional structure is now a common approach in the identification of new lead compounds. This "virtual screening" approach relies on fast and accurate estimation of the ligand binding mode and an estimate of ligand affinity. Typically a large database of compounds, either real or virtual is docked to a target structure and a list of the best potential ligands is produced. This ranking should be highly enriched for active compounds which may then be subject to further experimental validation.

The calculation of the ligand binding mode may be carried out by molecular docking programs which are able to dock the ligands in a flexible manner to a protein structure. The estimation of ligand affinity is typically carried out by the use of a separate scoring function. These scoring functions include energy-based approaches which calculate the molecular mechanics force field and rule-based approaches which use empirical rules derived from the analysis of a suitable database of structural information. Consensus scoring involves rescoring each ligand with multiple scoring functions and then using a combination of these rankings to generate a hit list.

SHORT DESCRIPTION OF TABLES 3-4

Table 3 shows the coordinates of an apo crystal of human IDE (amino acids 43-962, 987-1010, 46-962 and 987-1010 of Seq. Id. No. 2, respectively, in order of appearance) and Table 4 shows the coordinates of a co-crystal of human IDE (amino acids 43-962, 980-1010, 46-962 and 987-1010 of Seq. Id. No. 2, respectively, in order of appearance) with allosteric ligand 1H-Indole-7-carboxylic acid (3-chloro-phenyl)-amide.

EXAMPLES

Example 1

Crystal Structure of apo Human IDE

Methods:
DNA Manipulation and Sequence Analysis
Preparation of DNA probes, digestion with restriction endonucleases, DNA ligation and transformation of *E. coli* strains were performed as described (Sambrook, J., Fritsch, E. F. & Maniatis, T. (1989). Molecular Cloning: A Laboratory Manual. Cold Spring Harbor Laboratory Press: Cold Spring Harbor, N.Y.). Mutagenesis was performed by using the QuikChange Multi Kit from Stratagene. For DNA sequencing, the ABI PRISM BigDye Terminator Cycle Sequencing Ready Reaction Kit and ABI PRISM 310 Genetic analyzer were used. PCR were performed in the T3 Thermocycler (Whatman Biometra), using the iProof polymerase (Biorad).

Cloning and Purification
The human IDE gene (Seq. Id. No. 1), amino acids 43-1018 of Seq. Id. No. 2, was amplified by PCR from a cDNA clone. We utilized overlapping extension PCR to remove two internal NdeI-sites. In a second PCR with oligonucleotides 5'-GC-CATATGAATAATCCAGCC ATCAAGAG (Seq. Id. No. 3) and 5'-GCTGCGGCCGCTCAGAGTTTTGCAGCCATG (Seq. Id. No. 4) a NdeI site at the N-terminus and a NotI-site at the C-terminus were introduced. The resulting DNA fragment was cloned into the vector pET28 to create a fusion with a N-terminal His-tag. pERI-hIDE (43-1018) was transformed into the *E. coli* strain Bl21(DE3) and expressed at 20° C.

Purification
Cells were resuspended in 50 mM Tris/HCl pH 7.8, 500 mM NaCl, 2 mM TCEP, 10% Glycerin 2 mM MgCl2 and 2 mM DFP. Every 10 ml cell suspension was supplemented with 1 tablet Roche Complete Protease inhibitor mix and 0.2 mg DNAse I. Cells are then disrupted with a cell homogenizer at 800 bar and centrifuged at 34000×g for 90 min at 4° C. The supernatant was filtered through a 0.22 μm membrane, applied onto a His-select column further purified by anion exchange chromatography. Three peaks were obtained and separately concentrated and further purified on a Superose 6 column by size exclusion chromatography equilibrated with 50 mM Tris/HCl pH 7.8, 100 mM NaCl, 3 mM TCEP, and 10% glycerol. The three pools obtained had a purity of more than 90%, but differed in monodispersity and specific activity. The hIDE eluted at lower salt concentration (50 mM) is monodisperse and exhibits the highest specific activity. hIDE eluted at higher salt concentration (250 mM) shows approximately only half of the specific activity of pool 1 and is polydisperse with respect to analytical ultracentrifugation. All three pools are virtually identical on HPLC, SDS-PAGE and IEF.

Crystallization and Structure Determination:

hIDE has been purified as described above. The protein was concentrated to 11 mg/ml and prior to crystallization setups centrifuged at 20000×g for 10 min. The crystallization droplet was set up at 4° C. by mixing 1.5 µl of protein solution with 0.5 µl reservoir and 0.3 µl of a seed stock solution in vapour diffusion hanging drop experiments. Crystals appeared out of 100 mM Tris/HCl pH 8.5, 200 mM ammonium acetate, 25% PEG5000 MME and 10% ethylene glycol after 1 day and grew to a final size of 0.2×0.1×0.05 mm within 3 days. The seed crystals were prepared directly in the crystallization solution.

Crystals were harvested with 20% ethylene glycol as cryoprotectant and then flash frozen in a 100K N2 stream. Diffraction images were collected at a temperature of 100K at the beamline X10SA of the Swiss Light Source and processed with the programs MOSFLM and SCALA (CCP4) yielding data to 2.3 Å resolution. As alternative to obtain phase information and to determine the structure by MAD experiments selenomethionine labeled protein was crystallized in the P21 crystal form and data collected at three wavelengths from one crystal at the SLS (17.12.2005). 45 out of 46 selenium sites could be located by use of the program autoSHARP. The electron density obtained was of good quality extending to 3.5 Å. Into the density a polyalanine model for one monomer was build. This incomplete model was then used to do molecular replacement on a dataset of a native crystal extending to higher resolution (2.3 Å). Automatic model building with ArpWarp and manual rebuilding of about 500 amino acids was needed to finish the structure. Standard crystallographic programs from the CCP4 software suite were used to determine the structure by molecular replacement and for refinement (CCP4 (Collaborative Computational Project, N. The CCP4 suite: programs for protein crystallography. Acta Crystallogr. D 50, 760-763 (1994)). Refinement and model building cycles were performed with REFMAC and MOLOC, respectively (Table 1).

Results:

The crystals belong to space group $P2_1$ with cell axes a=78.5 Å, b=115.9 Å, c=124.0 Å, β=97.9° and diffracted to 2.3 Å resolution. The asymmetric unit is formed by an IDE dimer. IDE folds into four domains with domain 1 containing the active site. The four domains enclose a cavity with a diameter of about 40 Å. Two histidine and two glutamic acid side chains and one water molecule co-ordinate the $Zn^{2+}$ ion and form the active site which is located at the inner wall of the cavity.

TABLE 1

Data collection and structure refinement statistics for apo hIDE

Data Collection

| | |
|---|---|
| Wavelength (Å) | 1.008 |
| Resolution[1] (Å) | 2.3 (2.42-2.3) |
| Unique reflections[1] | 92628 |
| Completeness (%)[1] | 99.9 (100) |
| $R_{merge}$ (%)[1,2] | 7.3 (25.5) |
| $<I/\sigma>$[1] | 7.7 (2.8) |
| Unit Cell (Space group $P2_1$) | a = 78.5 Å, b = 115.9 Å, c = 124.0 Å, β = 97.9° |

TABLE 1-continued

Data collection and structure refinement statistics for apo hIDE

Refinement

| | |
|---|---|
| Resolution (Å) | 2.3 (2.36-2.3) |
| $R_{cryst}$[1,3] | 17.9 (18.8) |
| $R_{free}$[1,4] | 24.1 (28.6) |
| R.m.s. deviations from ideality Bond lengths (Å)/angles (°) | 0.015/1.459 |
| Main chain dihedral angles (%) Most favored/allowed/generous/disallowed[5] | 91.7/8.3/0.0/0.0 |

[1]Values in parentheses refer to the highest resolution bins.
[2]$R_{merge}$ = I-<I>/I where I is the reflection intensity.
[3]$R_{cryst}$ = Fo-<Fc>/Fo where Fo is the observed and Fc is the calculated structure factor amplitude.
[4]$R_{free}$ was calculated based on 5% of the total data omitted during refinement.
[5]Calculated with PROCHECK [Laskowski, R. A., MacArthur, M. W., Moss, D. S. & Thornton, J. M. PROCHECK: a program to check the stereochemical quality of protein structure. J. Appl. Crystallogr. 26, 283-291 (1993)].

Example 2

Crystal Structure of Human IDE with
1H-Indole-7-Carboxylic Acid
(3-Chloro-Phenyl)-Amide Purification:

Purification see first example.

Crystallization and Structure Determination:

hIDE has been purified as described above. Protein at a concentration of 1 M was incubated with 5 M ligand. Prior to crystallization setups the protein was concentrated to 12 mg/ml and centrifuged at 20000×g for 10 min. The crystallization droplet was set up at 4° C. by mixing 1.5 µl of protein solution with 0.5 µl reservoir and 0.5 µl of a seed stock solution in vapour diffusion hanging drop experiments. Crystals appeared out of 100 mM Bis-Tris pH 6.5, 200 mM ammonium acetate, 20% PEG 1500, 4% PEG 400 and 10% ethylene glycol after 1 day and grew to a final size of 0.2×0.1×0.05 mm within 3 days. The seed crystals were prepared in the crystallization solution.

Crystals were harvested with 20% ethylene glycol as cryoprotectant and then flash frozen in a 100K N2 stream. Diffraction images were collected at a temperature of 100K at the beamline X10SA of the Swiss Light Source and processed with the programs MOSFLM and SCALA (CCP4) yielding data to 1.7 Å resolution.

Standard crystallographic programs from the CCP4 software suite were used to determine the structure and for refinement (CCP4 (Collaborative Computational Project, N. The CCP4 suite: programs for protein crystallography. Acta Crystallogr. D 50, 760-763 (1994)). Refinement and model building cycles were performed with REFMAC and MOLOC, respectively (Table 2).

Results:

The allosteric pocket is located about 10 Å away from the active site. The indole of the indole carboxamide class binds here with the amide involved in hydrogen bonding via water molecules to IDE and the aromatic ring with the Cl-substituent points towards the inner cavity and probably to the substrate. The allosteric binding site is formed by residues L201, F202, Q203, L204, K205, T208, Y302, I304, Y314, V315, T316, F317, E364, I374, N376, R472, V478, A479, V481.

TABLE 2

Data collection and structure refinement statistics for hIDE with
1H-Indole-7-carboxylic acid (3-chloro-phenyl)-amide

| Data Collection | hIDE with 1H-Indole-7-carboxylic acid (3-chloro-phenyl)-amide |
|---|---|
| Wavelength (Å) | 0.95370 |
| Resolution[1] (Å) | 1.7 (1.79-1.7) |
| Unique reflections[1] | 215456 |
| Completeness (%)[1] | 89.2 (55.8) |
| $R_{merge}$ (%)[1,2] | 8.4 (74.2) |
| $<I/\sigma>$[1] | 5.4 (1.2) |
| Unit Cell (Space group P2$_1$) | a = 78.9 Å, b = 115.8 Å, c = 123.8 Å, β = 97.8° |
| Refinement | |
| Resolution (Å) | 1.7 (1.744-1.7) |
| $R_{cryst}$[1,3] | 19.4 (31.0) |
| $R_{free}$[1,4] | 23.3 (31.8) |
| R.m.s. deviations from ideality Bond lengths (Å)/angles (°) | 0.013/1.313 |
| Main chain dihedral angles (%) Most favored/allowed/generous/disallowed[5] | 92.5/7.4/0.1/0.0 |

[1]Values in parentheses refer to the highest resolution bins.
[2]$R_{merge}$ = I-<I>/I where I is the reflection intensity.
[3]$R_{cryst}$ = Fo-<Fc>/Fo where Fo is the observed and Fc is the calculated structure factor amplitude.
[4]$R_{free}$ was calculated based on 5% of the total data omitted during refinement.
[5]Calculated with PROCHECK [Laskowski, R. A., MacArthur, M. W., Moss, D. S. & Thornton, J. M. PROCHECK: a program to check the stereochemical quality of protein structure. J. Appl. Crystallogr. 26, 283-291 (1993)].

The invention claimed is:

1. An apo crystal of an insulin-degrading enzyme (IDE) polypeptide, wherein the crystal belongs to space group $P2_1$, and wherein further the IDE polypeptide comprises amino acids 43-1018 of SEQ ID NO:2, and wherein further the crystal has unit cell dimensions of a=78±3 Å, b=115±3 Å, c=124±3 Å, β=97±3°.

2. A co-crystal of an insulin-degrading enzyme (IDE) polypeptide and an allosteric Ligand, wherein
   a) the crystal belongs to space group $P2_1$ and has unit cell dimensions of a=78±3 Å, b=115±3 Å, c=123±3 Å, β=97±3°,
   b) the IDE polypeptide comprises amino acids 43-1018 of SEQ ID NO:2 and
   c) the allosteric Ligand is 1H-Indole-7-carboxylic acid (3-chloro-phenyl)-amide.

3. A method of crystallizing an insulin-degrading enzyme (IDE) polypeptide, the method comprising:
   a) providing an 11 mg/ml aqueous solution of the IDE polypeptide, wherein said IDE polypeptide is a polypeptide comprising a sequence having an identity to a polypeptide of SEQ ID NO: 2 of at least 95%, and
   b) growing crystals by vapor diffusion or microbath at 4° C. via mixing 1.5 ul of the IDE protein solution with 0.3 ul of a seed stock solution and 0.5 ul of a reservoir solution, wherein said buffered reservoir solution comprises 100 mM Tris/HCl pH 8.5, 200 mM ammonium acetate, 25% (w/v) PEG5000 MME and 10% ethylene glycol.

4. A method for co-crystallizing an insulin-degrading enzyme (IDE) polypeptide with an allosteric Ligand, the method comprising:
   a) providing an 12 mg/ml aqueous solution of the IDE polypeptide, wherein said IDE polypeptide is a polypeptide comprising a sequence having an identity to a polypeptide of SEQ ID NO: 2 of at least 95%, and
   b) adding a molar excess of the allosteric Ligand to the aqueous solution of the polypeptide, wherein the allosteric Ligand is 1H-Indole-7-carboxylic acid (3-chloro-phenyl)-amide and
   c) growing crystals by vapor diffusion or microbath at 4° C. using via mixing 1.5 ul of the IDE protein solution with 0.5 ul of a seed stock solution and 0.5 ul of a reservoir solution, wherein said buffered reservoir solution comprises 100 mM Bis-Tris/HCl pH 6.5, 200 mM ammonium acetate, 25% (w/v) PEG1500, 4% PEG 400 and 10% ethylene glycol.

* * * * *